United States Patent
Li et al.

(10) Patent No.: US 11,796,457 B1
(45) Date of Patent: Oct. 24, 2023

(54) ROOM TEMPERATURE OXYGEN SENSORS

(71) Applicant: United States of America as Represented by the Administrator of NASA, Washington, DC (US)

(72) Inventors: Jing Li, San Jose, CA (US); Kevin Kailin Du, San Jose, CA (US)

(73) Assignee: United States of America as Represented by the Administrator of NASA

( * ) Notice: Subject to any disclaimer, the term of this patent is extended or adjusted under 35 U.S.C. 154(b) by 116 days.

(21) Appl. No.: 17/138,806

(22) Filed: Dec. 30, 2020

(51) Int. Cl.
- *C12N 15/10* (2006.01)
- *B01L 3/00* (2006.01)
- *G01N 21/3504* (2014.01)
- *G01N 33/00* (2006.01)

(52) U.S. Cl.
CPC ..... *G01N 21/3504* (2013.01); *G01N 33/0039* (2013.01)

(58) Field of Classification Search
CPC .............. G01N 21/3504; G01N 33/0039
See application file for complete search history.

(56) References Cited

FOREIGN PATENT DOCUMENTS

CN 110822580 A * 2/2020

* cited by examiner

*Primary Examiner* — Jennifer Wecker
*Assistant Examiner* — Oyeleye Alexander Alabi
(74) *Attorney, Agent, or Firm* — Rhys W. Cheung; Robert M. Padilla; Trenton J. Roche

(57) ABSTRACT

Highly accurate oxygen sensors made of graphene and titanium dioxide hybrid material are provided. With UV illumination, the disclosed sensors are capable of detecting $O_2$ gas at room temperature and ambient pressure. The sensors are able to detect oxygen at concentrations ranging from about 0.2% to about 10% by volume under 365 nm UV light, and at concentrations ranging from 0.4% to 20% by volume under short wave UV light. The disclosed sensors have fast response and recovery times and can also be used to detect ozone.

17 Claims, 17 Drawing Sheets

(a)

ROOM TEMPERATURE OXYGEN SENSORS

ORIGIN OF INVENTION

The invention described herein was made in the performance of work under a NASA contract and by (an) employee(s) of the United States Government and is subject to the provisions of Public Law 96-517 (35 U.S.C. § 202) and may be manufactured and used by or for the Government for governmental purposes without the payment of any royalties thereon or therefore. In accordance with 35 U.S.C. § 202, the contractor has elected not to retain title.

FIELD

Provided herein are graphene and titanium dioxide oxygen sensors capable of detecting $O_2$ gas at room temperature and ambient pressure. The disclosed sensors may be used for environmental monitoring, medical applications, food processing, steel and cement production, ink-jet, and laboratory safety, and they can be easily prepared from solution-phase synthesized graphene and titanium oxide hybrid materials for mass production.

BACKGROUND

Oxygen ($O_2$) gas sensors measure the proportion of oxygen in gas and are widely used for combustion engine and environmental monitoring, medical applications, food processing, steel and cement production, and laboratory safety. Oxygen sensors are usually made of metal-oxides, such as $In_2O_3$, $SnO_2$, ZnO, or yttria-stabilized zirconia. Traditional $O_2$ gas sensors were based on the principles of potentiometric equilibrium or limiting current amperometry. Different technologies are now used to measure oxygen, including zirconia, electrochemical, infrared, ultrasonic, paramagnetic and laser methods. Semiconducting gas sensors experience changes in resistance when exposed to certain gases.

Graphene is a two-dimensional monolayer of $sp^2$-bonded carbon atoms, and it is an ideal material to use as a gas sensor because of its high surface area-to-volume ratio, high carrier mobility and low electrical noise. Graphene experiences a change in resistance when gas molecules are adsorbed on its surface. The magnitude and direction of these resistance changes depend on the type of gas and its concentration. Types of graphene include mechanically exfoliated graphite, reduced graphene oxide (rGO), and graphene grown by chemical vapor deposition (CVD). Graphene sensors have shown remarkable sensitivity to some gases, such as $NO_2$ and $NH_3$. Furthermore, rGO is very sensitive to certain chemical warfare agents, such as dimethyl methylphosphonate (DMMP) and 2-chloroethyl ethyl sulfide (CEES). However, graphene is not inherently sensitive to $O_2$ gas.

Titanium dioxide ($TiO_2$) is an n-type semiconducting material and, similar to graphene, its electrical resistance changes upon adsorption of an analyte gas. Titanium dioxide has wide use in air-fuel sensors for automobiles since it is inexpensive, non-toxic, and very stable. However, the use of titanium dioxide as a gas sensor is limited, because $TiO_2$ is only functional at very high temperatures (about 300° C.).

Graphene-$TiO_2$ hybrids exhibit fast and efficient charge separation at the interface and have desirable photocatalytic properties under UV light. However, the development of graphene-$TiO_2$ hybrids is a very expensive process, and it is not suitable for mass production. Cost-effective methods of producing graphene-$TiO_2$ hybrids are therefore needed.

SUMMARY

The present application presents a solution to the aforementioned challenges by providing a cost-effective and easily scalable technique for producing graphene-$TiO_2$ oxygen sensors. The methods provided herein make use of solution-phase synthesized graphene-$TiO_2$ hybrid materials that are ultrasonicated and drop-casted onto a series of inter-digitated electrodes (IDE). The disclosed methodology, which is cost-effective and easy to scale up for mass production, is able to produce accurate and reliable oxygen sensors that, unlike traditional metal-oxide sensors, are functional at room temperature and can be integrated into wearable-size IoT devices. The oxygen sensors provided herein thus require little energy and may be used for environmental monitoring, medical applications, food processing, steel and cement production, and laboratory safety. Oxygen sensors that are functional at room temperature and ambient pressure, and methods for producing the disclosed sensors and for accurate determination of oxygen and ozone in gaseous samples are provided.

Thus, in some embodiments, provided herein is a gas sensor that detects oxygen gas at room temperature. The disclosed sensor comprises titanium dioxide nanoparticles attached to graphene nanoplatelets.

The graphene nanoplatelets and the titanium dioxide nanoparticles are in a weight ratio from about 55:45 to about 75:25. In some embodiments, the graphene nanoplatelets and the titanium dioxide nanoparticles are in a weight ratio of about 70:30.

The disclosed sensor may be integrated into an artificial intelligence device.

In some embodiments, the disclosed oxygen sensor has a resistance that changes in oxygen's presence upon exposure to UV light.

Also provided herein is a method of producing a gas sensor that detects oxygen at room temperature. The disclosed method comprises: (i) mixing graphene nanoplatelets and titanium dioxide ($TiO_2$) nanoparticles to obtain a dispersion; (ii) ultrasonicating the dispersion to obtain a homogeneous graphene-$TiO_2$ dispersion; and (iii) drop-casting the homogeneous graphene-$TiO_2$ dispersion onto an integrated electronics (IDE) channel on a printed circuit board (PCB) sensor chip.

The graphene nanoplatelets may have an average surface area of 600 to 750 $m^2$/g, a thickness of about 5-10 nm, and a diameter of 1-5 μm. The titanium dioxide nanoparticles may have an average particle size of about 5 nm to about 15 nm.

The graphene nanoplatelets and the titanium dioxide nanoparticles may be mixed in a weight ratio from about 55:45 to about 75:25. In some embodiments, the graphene nanoplatelets and the titanium dioxide nanoparticles are mixed in a weight ratio of about 70:30.

In some embodiments, the disclosed method comprises mass-producing the sensor by wafer fabrication, and it may further comprises integrating the sensor into an artificial intelligence device.

The sensors produced by the disclosed method change resistance in oxygen's presence upon exposure to a UV light source.

Additionally provided herein is a method of detecting an analyte in a gaseous sample at room temperature and ambient pressure. The disclosed method comprises: (i) exposing a gas sensor to a gaseous sample, wherein the gas sensor comprises titanium oxide nanoparticles attached to graphene nanoplatelets; (ii) exposing the sensor to UV irradiation at room temperature; and (iii) measuring a change in the sensor's resistance in response to UV irradiation, wherein magnitude of the change in the sensor's resistance is dependent upon the analyte's concentration, thereby detecting the analyte in the gaseous sample.

The disclosed method may further comprise determining the concentration of the analyte in the sample according to the logarithmic formula: $S=0.0107 \ln C+0.0321$, wherein S is the change in the sensor's resistance in response to UV irradiation defined as: $S=(R-R_0)/R_0$, wherein $R_0$ is the sensor's base resistance and R is the sensor's resistance measured during gas exposure, and C is the concentration of the analyte in the gaseous sample.

In some embodiments, the disclosed method may further comprise purging the sensor with nitrogen for a time period from about 1 minute to about 20 minutes to decrease the sensor's resistance to baseline after each exposure to UV light.

In some embodiments, the sensor's change in resistance time in response to UV irradiation is about 250 seconds, and the sensor's recovery time is about 640 seconds.

In some embodiments, the UV irradiation is long wave UV light, and the analyte is oxygen. The long wave UV light may be a 365 nm UV light, and upon UV irradiation the sensor's resistance increases with an increase in oxygen concentration in the gaseous sample.

In some embodiments, the sensor may detect an oxygen concentration in the gaseous sample that is in a range from about 0.06% to about 15% (v/v).

In some embodiments, the UV irradiation is short wave UV light, and the analyte is oxygen and/or ozone. The short wave UV light may be a 254 nm UV light, and upon UV irradiation the sensor's resistance decreases with an increase in oxygen concentration in the gaseous sample.

In some embodiments, the sensor may detect an oxygen concentration in the gaseous sample that is in a range from about 0.4% to about 21.5% (v/v).

In some embodiments, the gas flow is kept constant at 400 sc/cm.

The graphene nanoplatelets and the titanium dioxide nanoparticles in the disclosed sensors may be in a weight ratio from about 55:45 to about 75:25. In some embodiments, the graphene nanoplatelets and the titanium dioxide nanoparticles are in a weight ratio of about 70:30.

In some embodiments, the disclosed method may comprise alternatively irradiating the sensor with a long wave UV light source and a short wave UV light source in order to detect both oxygen and ozone in the surrounding environment. The long wave UV light may be a 365 nm UV light, and the short wave UV light may be a 254 nm UV light. In some embodiments, the UV light source is a light emitting diode (LED).

In some embodiments, the sensor is integrated into an artificial intelligence device.

In some embodiments, the gaseous sample is a spacecraft sample, a spacesuit sample, a food processing sample, a steel or cement production sample, an ink jet sample, a solution casting sample, a spin-coating sample, a laboratory sample, an electronic fuel injection or emission sample, a medical sample, or a pharmaceutical sample.

The foregoing and other features of the disclosure will become more apparent from the following detailed description of several embodiments, which proceeds with reference to the accompanying figures.

DETAILED DESCRIPTION

Figure 1:
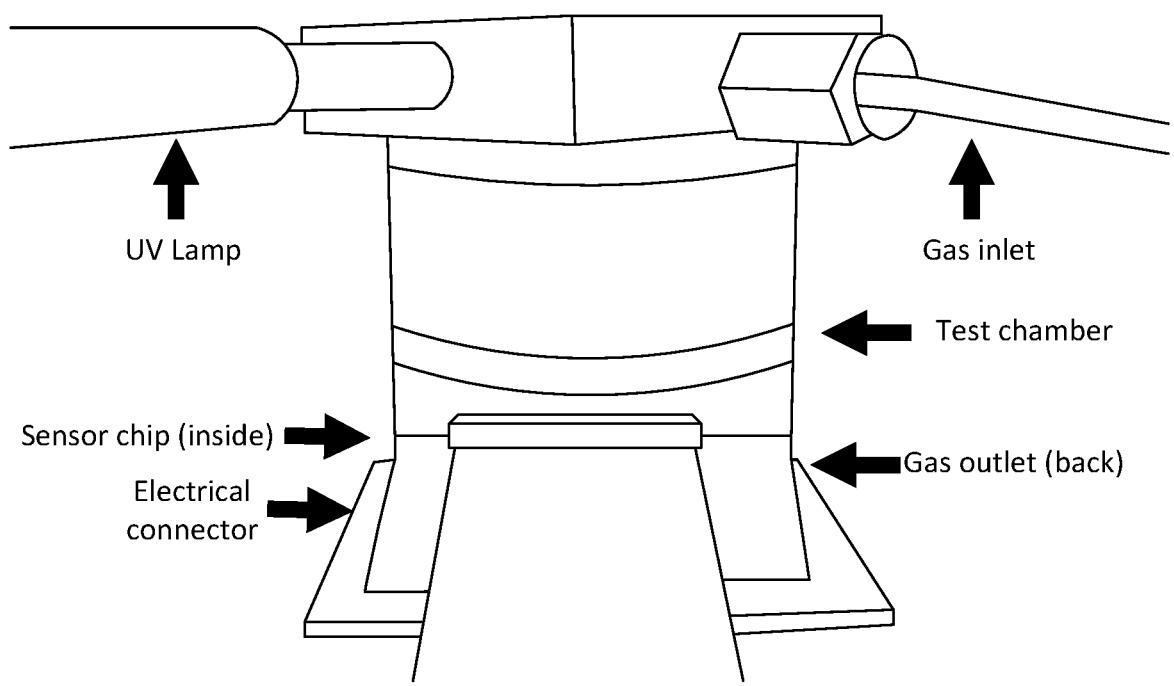
FIG. 1 shows the system used to measure oxygen sensing at room temperature and atmospheric pressure.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein.

Unless explained otherwise, all technical and scientific terms used herein have the same meaning as commonly understood to one of ordinary skill in the art to which this disclosure belongs. The materials, methods, and examples are illustrative only and not intended to be limiting.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties for a particular embodiment. The recitation of ranges of values herein is merely intended to serve as a shorthand method of referring individually to each separate value falling within the range. To facilitate review of the various embodiments of this disclosure, the following explanations of specific terms are provided:

Analog: A compound having a structure similar to another, but differing from it, for example, in one or more atoms, functional groups, or substructure.

Chemical Sensor: A measurement device that converts a chemical or physical property of a specific analyte into a measurable signal, whose magnitude is proportional to the concentration of the analyte. Chemical sensors can use capacitive readout cantilevers and electronics to analyze a transmitted signal and change one or more electrical characteristics, such as resistance, upon absorbing a gas molecule.

Contacting: Placing a substance in direct physical association with a material in solid, liquid, or gas form.

Control: A reference standard of a known value or range of values.

Graphene: An allotrope of carbon consisting of a single layer of atoms arranged in two-dimensional honeycomb lattice. Among its uses are anti-corrosion coatings and paints, sensors, electronics, displays, solar panels, drug delivery and DNA sequencing.

Hybrid Material: A composite consisting of two or more components that are combined into a matrix at nanometer or molecular level. In some cases, one component is inorganic, and one component is organic. Hybrid nanocomposites can include technological platforms used in photovoltaic cells and light-emitting devices, lithium ion batteries, supercapacitors and sensors.

Metal Oxide: A crystalline solid catalyst that contains a metal cation and an oxide anion, and reacts with water to form a base, or with an acid to form a salt. Metal oxides include, but are not limited to, carbon oxide, iron oxide, nitrogen oxide, silicon oxide, titanium oxide and aluminum oxide. Metal oxides can be used for example in sensor and biosensor applications, and their surface properties determine sensor's sensitivity.

Microchip: A unit of an integrated circuit made of silicon, germanium or other semiconducting material and used for program logic and computer memory.

Oxygen Sensor: An electronic device that measures the properties of oxygen in a gas or in a liquid.

Resistance: An electrical property that can be used to indicate a decrease in electric current flow through a device or material. Electrical resistance is defined as the ratio between the voltage applied to the electric current and the electric current that flows through it. If the resistance is constant over a considerable range of voltage, Ohm's law, $I=V/R$ can be used to predict a behavior of a material. An electric current flows when electrons move through a conductor. Factors that affect resistance include the type of material, length and thickness of the resistor and the temperature of the conductor.

Semiconductor: A material that has a conductivity between the conductivity of an insulator and the conductivity of most metals. The resistance of a semiconductor decreases as its temperature rises. Electronic devices that use semiconductors include, but are not limited to, diodes, transistors and integrated circuits.

Titanium Dioxide: The naturally occurring oxide of titanium found in ilmenite, and the minerals rutile and anatase. It is used for example in paint, paper, plastic, cosmetics, sunscreen and food coloring. Naosized titanium dioxide exhibits photocatalytic activity under UV irradiation.

Wafer Fabrication: A technology producing electrical or photonic circuits from semiconductor wafers. Examples include, but are not limited to, production of radio frequency amplifiers, LEDs, and computer components. The process may involve photomasking photoresist patterns onto the wafer's surface, exposing the wafers to UV light, cleaning away the unexposed area, depositing chemical vapors and heating at high temperatures.

Room Temperature Oxygen Sensors and Methods of Production and Detection

Oxygen sensors find use in a wide array of applications, including electronic fuel injection and emissions control in the automotive industry, oxygen monitoring for medical and pharmaceutical applications, environment control in spacecraft and spacesuits technology, food processing, steel and cement production, ink jetting, solution casting, spin-coating, and laboratory safety. Traditional oxygen sensors, including potentiometric and amperometric sensor designs, have significant drawbacks, as metal oxide gas sensors require a temperature of about 300° C. and suffer from high power consumption. Graphene sensors, including mechanically exfoliated graphite, reduced graphene oxide, and graphene grown by chemical vapor deposition, have recently been explored as alternatives to address these drawbacks. However, while graphene sensors are sensitive to a variety of gases, such as nitrogen dioxide and ammonia, they are not suitable for detecting oxygen. Moreover, their expensive production makes graphene sensors unsuitable for mass production.

The present application overcomes these drawbacks by providing low-cost, low-power, mass-producible oxygen sensors with a small footprint that are capable of detecting oxygen gas at room temperature, and an efficient and inexpensive process for producing the disclosed sensors. The disclosed oxygen sensors have a footprint that is one-tenth the size of currently available commercial $O_2$ sensors, and may be integrated into wearable-size internet of things (IoT) devices. Accordingly, the disclosed oxygen sensors provide significant advantages over large-size traditional sensors that require high operating temperatures requirements and power of operation.

Since graphene is not intrinsically responsive to $O_2$, and $TiO_2$ is not responsive to oxygen at room temperature, the oxygen sensors provided herein are made of hybrid material produced by modifying graphene nanoplatelets with titanium dioxide nanoparticles by solution-phase synthesis. The graphene and the titanium dioxide may be present in the composite material in different ratios to ensure maximal oxygen detection. A suitable graphene: $TiO_2$ ratio range may vary from about 55:45 to about 75:25. In some embodiments, the graphene and the titanium dioxide are present in the composite material in a ratio of about 70:30.

In some embodiments, the synthesized graphene-$TiO_2$ hybrid material is ultrasonicated and then drop-casted onto a series of interdigitated electrodes (IDE). Ultrasonication ensures effective charge transfer at the graphene-$TiO_2$ interphase. This approach is cost-effective, easy to scale-up into mass production, and yields a semiconducting material whose resistance changes upon absorption of an analyte gas, such as oxygen. In addition, since the disclosed sensors are chip-based, they can be manufactured by wafer fabrication. The ability to produce a multitude of chips on a single wafer reduces costs significantly, and lends itself to automated manufacturing processes, which may reduce costs even further.

The sensors thus produced are exposed to UV light for gas detection.

Figure 10:
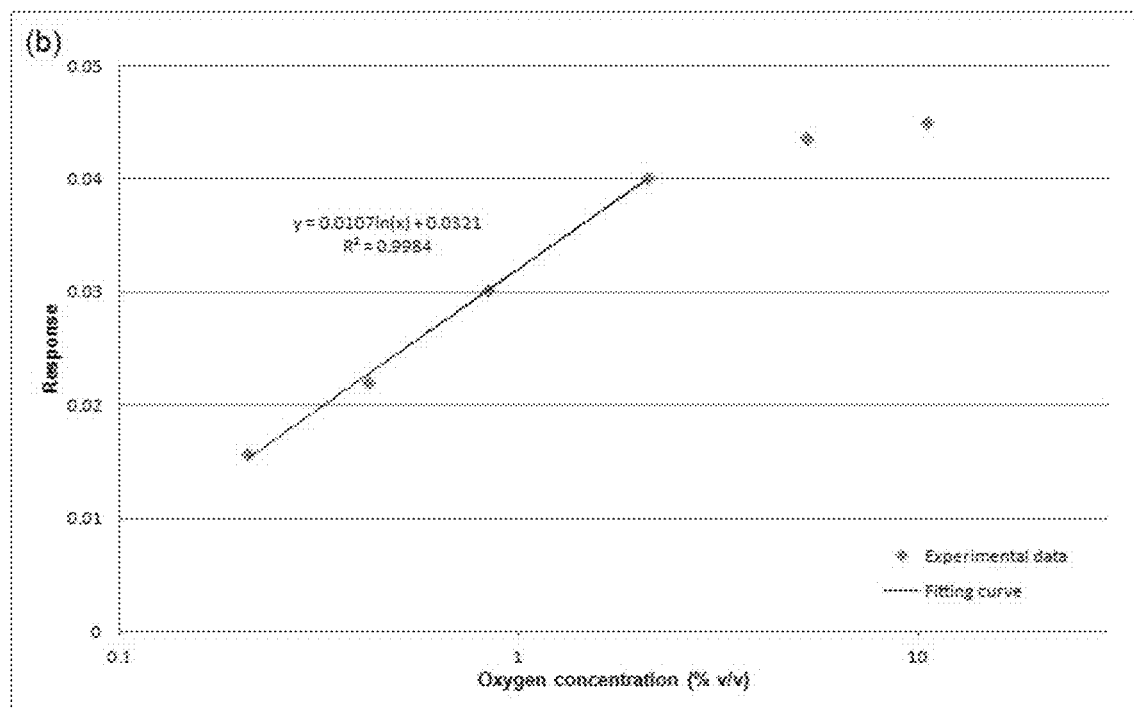
FIG. 10 is a calibration curve used to determine detection limits.

In some embodiments, the disclosed sensors may be used to detect low concentrations of oxygen. Oxygen gas detection is performed by exposing the disclosed sensors to long wave UV light at room temperature. A long wave UV light of 365 nm excites the graphene-$TiO_2$ sensors and causes the sensors' resistance to increase upon exposure to $O_2$ gas. Gas flow may be varied or kept constant. In some embodiments, the gas flow may be kept constant at 400 sc/cm. As shown in FIG. 10, the magnitude of the response signal under 365 nm UV light exposure is dependent upon the concentration of $O_2$ gas. Under such conditions, the disclosed sensors can detect $O_2$ gas according to the logarithmic formula: $S=0.0107 \ln C+0.0321$, wherein S is the response signal, and C is the oxygen concentration. The response signal, which is the relative resistance change of the sensor, is defined as: $S=(R-R_0)/R_0$, where $R_0$ is the base resistance of the sensor measured during the initial $N_2$ purge and R is the resistance measured during oxygen exposure. Thus, the disclosed sensors may detect oxygen at room temperature upon irradiation with 365 nm UV light in concentrations from about 0.06% v/v to about 21% v/v. Higher oxygen concentration may cause the sensor to become saturated with oxygen, and thus unresponsive.

In some embodiments, the disclosed sensors may be used to separately detect oxygen at high concentrations and ozone. Gas detection is performed by exposing the disclosed sensors to short wave UV light at room temperature. A short wave UV light of 254 nm causes the sensors' resistance to decrease upon exposure to $O_2$ gas in graphene and graphene-$TiO_2$ hybrid sensors. Under such conditions, the disclosed sensors can detect $O_2$ gas according to the logarithmic formula: $S=0.0107 \ln C+0.0321$. Thus, the disclosed sensors may detect oxygen at room temperature upon irradiation with 254 nm UV light in concentrations above about 2.1% v/v and up to about 20% v/v. Furthermore, the disclosed sensors may detect ozone gas that is emitted by the short wave UV light.

For gas detection, a UV source may be connected to a chamber containing an oxygen sensor as described herein, and the chamber is connected to a gas inlet. Exposure to a UV source may be through an opening, such as a circular opening of about 0.5 cm in diameter. The UV source and the gas inlet may be at a distance from about 1 cm to about 10 cm from the sensor to prevent heat emanated from the lamp from affecting the sensor. The temperature of the sensor surface y be kept constant at about 25° C. with an infrared thermometer.

The disclosed oxygen sensors may be purged with nitrogen after each exposure to UV light. Purging time may vary from about 1 minute to about 20 minutes. In some embodiments, purging time may be 15 minutes long. Sensor exposure to oxygen gas increases resistance, and sensors purging with $N_2$ gas causes the disclosed sensors to recover and their resistance decreases to initial baseline levels.

The disclosed sensors exhibit fast response times and fast recovery time. In some embodiment, their response time is about 250 seconds and their recovery time is about 640 seconds.

The disclosed graphene-$TiO_2$ sensors detect $O_2$ with high precision at volume concentrations below about 2.1% v/v upon exposure to 365 nm UV light, and at concentrations above about 2.1% v/v upon exposure to 254 nm UV light. Therefore, the disclosed sensors can be used with long wave and short wave UV light sources, which can be alternatively switched to increase the measurement range. Light emitting diodes are suitable because of their smaller size, lower power consumption, and better control over the emitted wavelength. Thus, the disclosed sensors are highly precise and reliable, provide effective oxygen detection at room temperature with low power, have a wide range of detection, a low detection limit, fast response times and recovery times, and can be mass-produced by cost-effective technology. In addition, the oxygen sensors provided herein have small size, can be integrated into artificial intelligence devices, and may be used for a wide spectrum of applications, including, but not limited to, environmental control in spacecraft and spacesuits, food processing, steel and cement production, ink jetting, solution casting, spin-coating, laboratory safety, electronic fuel injection and emissions control, and oxygen monitoring for medical and pharmaceutical applications.

Thus, unlike traditional existing technologies, the disclosed sensors and methodology allows accurate determination of oxygen gas in one simple assay, and particularly attractive to industry in applications that demand room-temperature operation, a very small footprint, and low production costs at scale.

EXAMPLES

Example 1: Sample Preparation and Sonication

Graphene nanoplatelets were purchased commercially in dry powder form and used as received. The nanoplatelets had an average surface area of 600 to 750 $m^2/g$, a thickness of 8 nm, and a diameter of 2 μm. Titanium dioxide nanoparticles were purchased from U.S. Research Nanomaterials and had an average particle size of 5 to 15 nm. The anatase form of $TiO_2$ was chosen because of its increased photocatalytic activity over the rutile form. The materials were mixed with deionized (DI) water in a vial at a concentration of 1 mg/ml with a total solvent volume of 4 ml. Several different weight ratios of graphene to $TiO_2$ were tested, including a sample without any $TiO_2$. A probe ultrasonicator operating at output wattage of 5 was used to sonicate the dispersion. The vial was placed inside a cold water bath at a temperature of 15° C., and the tip of the sonicator probe was submerged halfway into the vial. Each sample was sonicated for 5 minutes. Homogeneity of the dispersion increased after sonication, as evidenced by a visible increase in color opacity. The increase in opacity was due to the breaking of nanoparticle aggregates by acoustic cavitation during ultrasonication. The hybrid dispersion thus obtained was then drop-casted using a micropipette onto an integrated electronics (IDE) channel on a printed circuit board sensor chip.

Other deposition methods were also tested, in which the graphene and $TiO_2$ were drop-casted in two separate steps. The graphene was drop-casted first to provide a stable electrical connection with the surface of the sensor chip and the metal electrodes. Then the $TiO_2$ layer was drop-casted above the graphene layer for greater exposure to incident light. These sensors were tested by exposure to $O_2$ gas under 365 nm UV light, but they gave no response. Lack of response was likely due to ineffective charge transfer between the graphene layer and the $TiO_2$ layer following layer-by-layer deposition method. In contrast, sonicated samples successfully functioned as sensors, as ultrasonic synthesis caused strong physisorption between graphene and $TiO_2$.

To further define sonication parameters, several graphene-$TiO_2$ hybrid materials were synthesized by low-power bath sonication or mixing using a magnetic stirrer. The sensors developed by low-power sonication or by mixing did not show significant response to $O_2$ gas. These results indicated that sonication of graphene and $TiO_2$ together is vital for creating effective $O_2$ sensors. Sonication was then further optimized by determining the effects of power, time, and different solvents on $O_2$ sensor production.

In view of these results, and because some slight precipitation of the dispersion occurs over time, drop-casting was performed immediately after sonication. A set volume of 0.5 µl, determined to be the optimal volume for achieving a measurable resistance, was deposited onto each sensing channel. The sensor was then heated in a vacuum oven at 80° C. and under 40 mm Hg pressure for 10 minutes to completely evaporate the solvent.

Example 2: Hybrid Material Characterization

Figure 3:
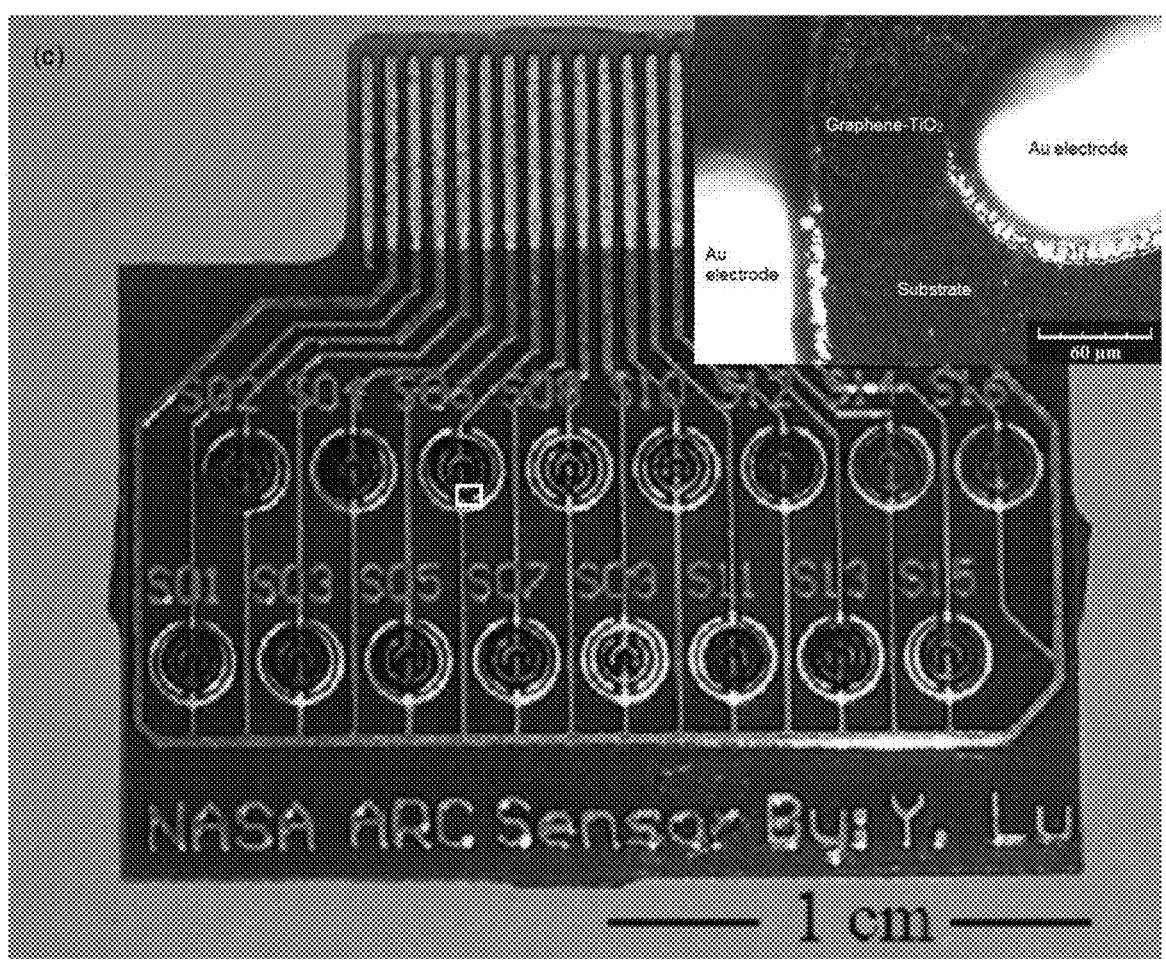
FIG. 3 shows sensor chips on which graphene-$TiO_2$ material was deposited. Each channel consisted of a pattern of gold electrodes having 80 µm finger width and 115 µm gap width. The inset shows an optical microscope image of an IDE channel on the sensor chip on which graphene-$TiO_2$ material had been deposited.

Optical microscope images of the sensor were taken, and surface characterization was done with a field emission scanning electron microscope (SEM) operating at an accelerating voltage of 5 kV. As shown in FIG. 3, a portion of the channel was covered with the graphene-$TiO_2$ hybrid material. This confirmed that the electrodes were bridged and the resistance of the hybrid material could be measured upon voltage application to the sensor chip.

Figure 4A:
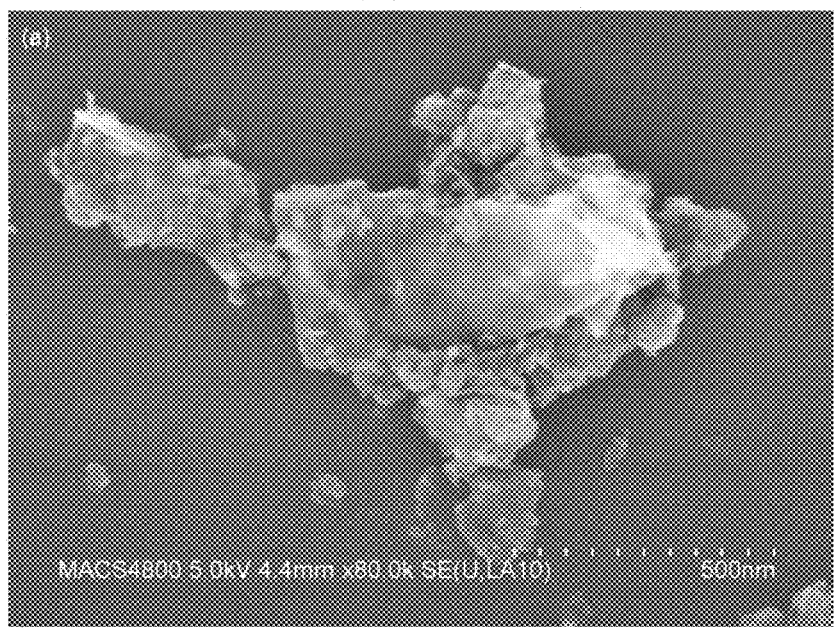
FIG. 4A shows a SEM image of a graphene nanoplatelet used in a sensor.

High magnification images were taken with a transmission electron microscope (TEM). Prior to TEM imaging, the dispersed material was drop-casted onto a copper mesh grid sample holder and heated. Raman spectra were obtained using a spectrometer with a 514.5 nm argon laser. For Raman and SEM characterization, the dispersed material was drop-casted onto a silica wafer shard and then heated in a vacuum oven to evaporate the solvent. Current-voltage (I-V) characteristic curve measurements were obtained using a semiconductor parameter analyzer. The SEM image in FIG. 4A shows an unmodified multilayer graphene nanoplatelet having an overall smooth surface with some irregular areas.

Figure 4B:
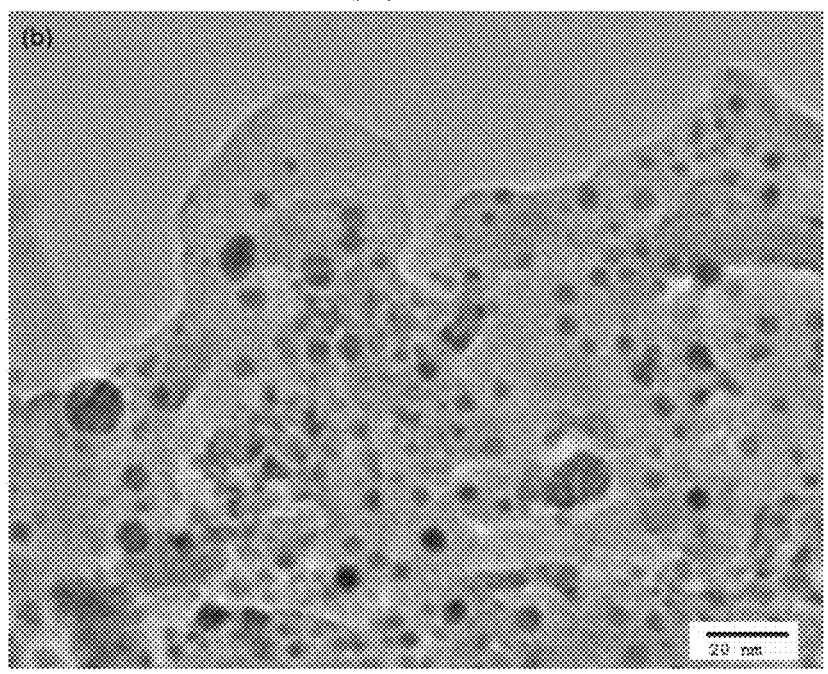
FIG. 4B is a TEM image of hybrid graphene-$TiO_2$ material showing individual $TiO_2$ nanoparticles attached to graphene surface.
Figure 5:
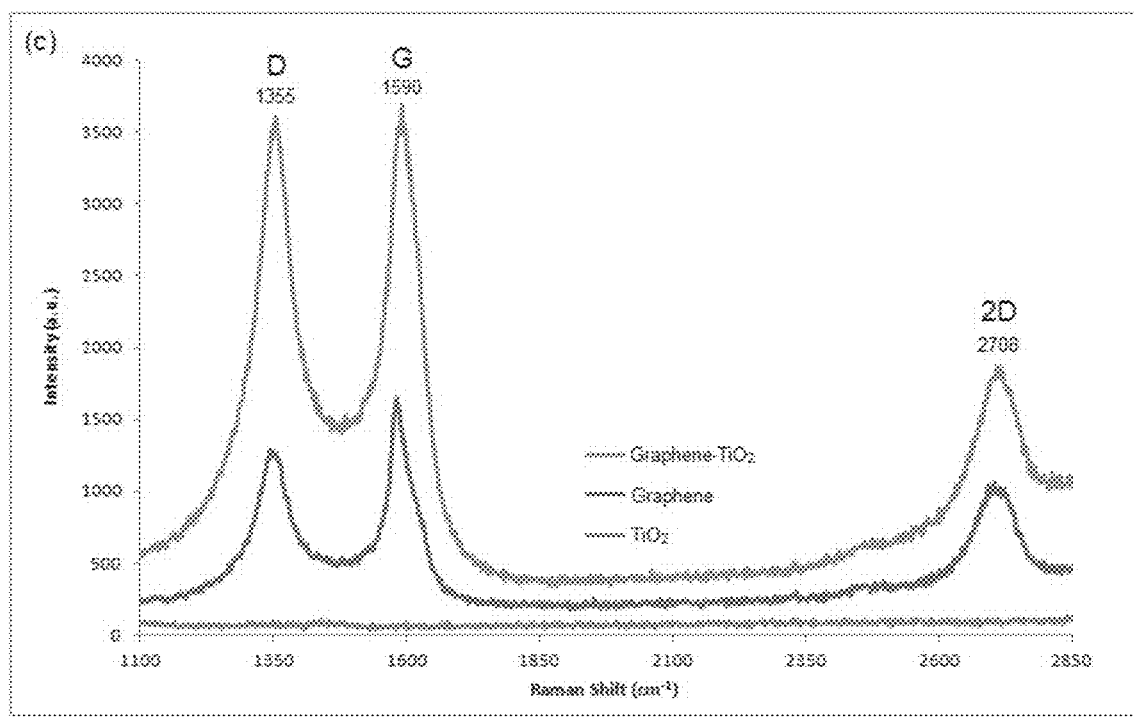
FIG. 5 shows Raman spectra for $TiO_2$ (bottom curve), graphene (middle curve) and graphene-$TiO_2$ hybrids (top curve).

TEM imaging was performed on a graphene-$TiO_2$ hybrid material having a 50:50 graphene to $TiO_2$ weight ratio. FIG. 4B shows a graphene nanoplatelet with $TiO_2$ nanoparticles evenly scattered through the graphene. The presence of $TiO_2$ on the graphene validates the feasibility of the ultrasonication procedure for synthesizing graphene-$TiO_2$ hybrid materials. Furthermore, the random distribution of the $TiO_2$ nanoparticles increases the surface area for UV excitation and $O_2$ adsorption. Raman spectroscopy was performed on the raw $TiO_2$ nanoparticles, the graphene nanoplatelets, and a hybrid material having a 25:75 graphene to $TiO_2$ weight ratio. The spectra shown in FIG. 2C show the position of the 2D peak at 2708 $cm^{-1}$. This data indicated that the graphene nanoplatelet had about six layers. The high intensity of the D band with respect to the G band suggested the presence of inherent defects in the graphene nanoplatelets and supported the findings from SEM imaging that an unmodified multilayer graphene nanoplatelet has an overall smooth surface with some irregular areas.

Comparative analysis of the raw $TiO_2$ spectra showed no peaks within the tested wave range. Addition of $TiO_2$ to graphene decreased the intensity ratio of the 2D band over the G band, and increased the intensity of the D band. These effects were attributed to electron doping of the graphene caused by addition of $TiO_2$.

Example 3: Gas Sensing Experiments

Gas sensing experiments were performed using the system shown in FIG. 1, using two different ultraviolet lamps: a long-wave lamp with a primary wavelength of 365 nm, and a short-wave lamp with a primary wavelength of 254 nm. One lamp at a time was each connected to a chamber with an interior volume of about 15 $cm^3$, which in turn was connected to a gas inlet. Exposure to each UV lamp was through a circular opening of about 0.5 cm in diameter. A distance of 5 cm from the lamp and gas inlet to the sensor was set to prevent heat emanated from the lamp from affecting the sensor. The temperature of the sensor surface was measured with an infrared thermometer and never exceeded 30° C. during the tests, such that any thermoelectric effects on sensor's resistance could be considered negligible. Keeping the gas inlet at a distance from the sensor also minimized the flow effect and resistance changes caused by the strain sensitivity of graphene. A gas outlet was located at the bottom of the chamber to prevent the pressure inside the chamber from exceeding atmospheric pressure.

Figure 2:
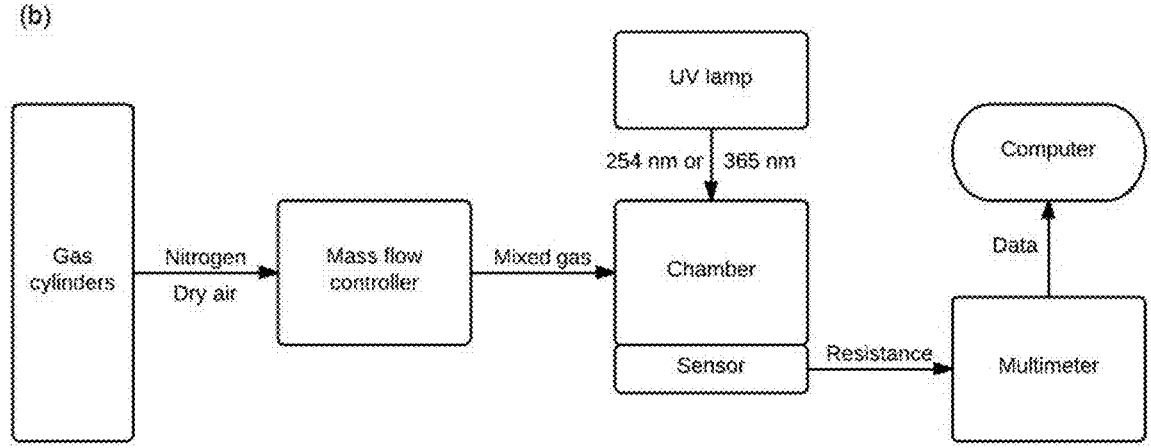
FIG. 2 is a diagram showing the procedural steps in oxygen sensing assays.
Figure 16:
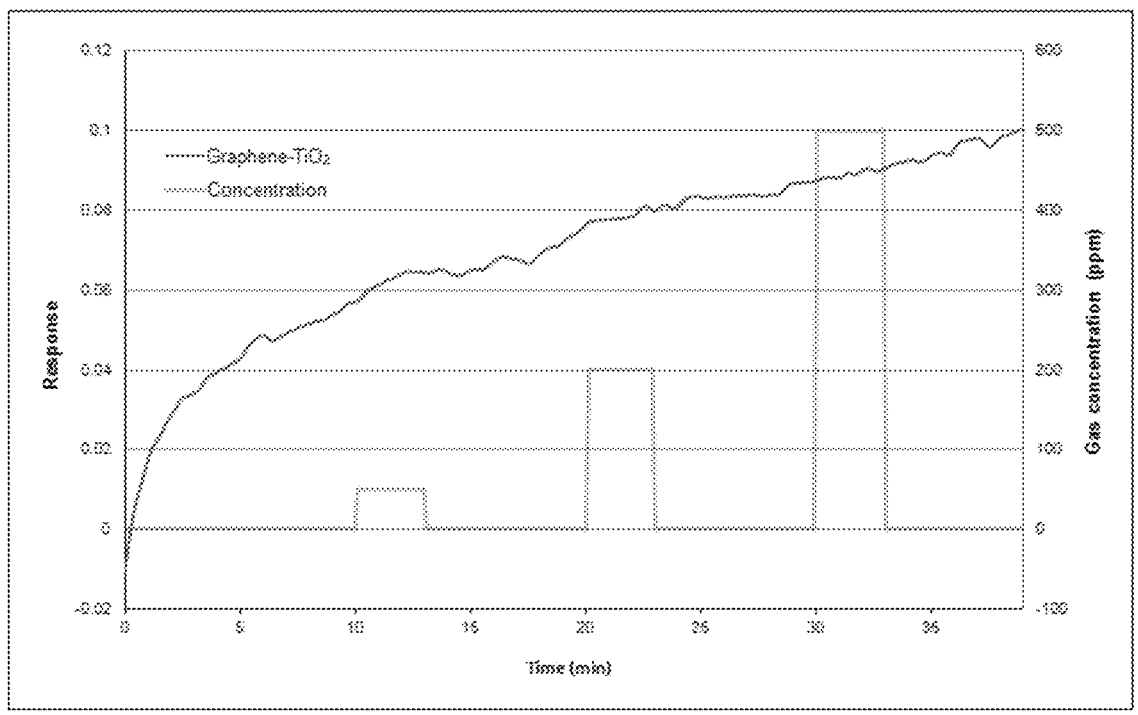
FIG. 16 shows carbon dioxide effect on graphene-$TiO_2$ sensors.

FIG. 2 shows a flow diagram of the gas sensing assays. A sensor chip on which the sensing material was deposited (FIG. 3) was placed inside the chamber and attached to a circuit board. The circuit board was then connected to a digital multimeter via an electrical connector with a ribbon cable. Resistance measurements were recorded onto a computer with a customized data acquisition program. A mass flow controller was used to blend gases and adjust the gas flow. To establish a baseline, pure nitrogen ($N_2$) gas was flowed into the chamber for 15 minutes to purge the sensor. Varying concentrations of dry air diluted in $N_2$ were then introduced over time with pure $N_2$ purging in between. Air was used to simulate $O_2$ in order to obtain lower concentrations of $O_2$ from the mass flow controller and to ensure that the sensor could operate in normal atmosphere without interference. The effects of carbon dioxide ($CO_2$) gas in air were ruled out by determining that sensor's exposure to increasing concentrations of $CO_2$ did not cause any resistance changes (FIG. 16). Gas flow was kept constant at 400 sc/cm and each UV lamp was turned on throughout each experiment.

Example 4: Exposure to 365 nm UV Light

The resistance of each sample produced as described above was measured prior to and following 5-minute exposure to 365 nm UV light in ambient air. The results summarized in Table 1 show a direct correlation between $TiO_2$ amount and resistance for each sample.

TABLE 1

Effect of 5-Minute Exposure to 365 nm UV Light on Sensors' Resistance in Ambient Air

| Graphene:TiO$_2$ Weight Ratio | Initial resistance ($\Omega$) | Resistance after exposure to UV light ($\Omega$) | Resistance change ($\Omega$) | Percent resistance change |
|---|---|---|---|---|
| 100:0 | 1534 | 1554 | 20 | 1.30% |
| 75:25 | 6550 | 7650 | 1100 | 16.79% |
| 70:30 | 10610 | 12840 | 2230 | 21.02% |
| 65:45 | 12030 | 15060 | 3030 | 25.19% |
| 60:40 | 27320 | 34270 | 6950 | 25.44% |
| 55:35 | 119000 | 155000 | 36000 | 30.25% |

Figure 6:
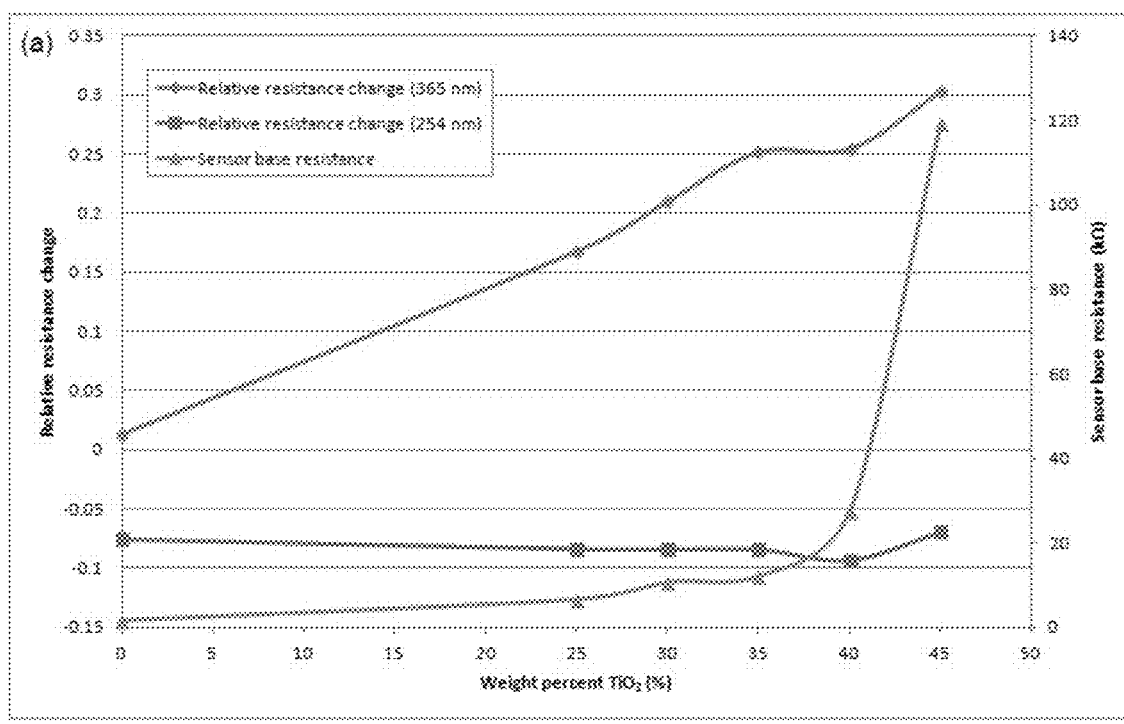
FIG. 6 is a graph depicting the effect of the graphene: $TiO_2$ weight ratio on sensors' base resistance of the sensor and relative resistance change upon UV exposure.

Increasing the ratio of TiO$_2$ in the samples further augmented the relative resistance increase upon UV exposure. When the data presented in Table 1 was plotted as shown in FIG. 6, the relative resistance induced by exposure to 365 nm UV light for each sample increased exponentially with TiO$_2$ increase, suggesting that further increasing the amount of TiO$_2$ in the hybrid material would significantly increase the base resistance.

A base resistance of about 10 k$\Omega$ is considered optimal for measuring electrical properties of a sensor (data not shown), as higher base resistance may cause drifting and lead to an unstable sensor. A base resistance greater than 10 M$\Omega$ is also not measurable with a multimeter. Therefore, when sensors with equal or more TiO$_2$ amount than graphene by weight were produced, their high resistance at room temperature rendered them unsuitable for sensor applications. Pure TiO$_2$ could also not be tested as a sensor, as the discontinuity between the nanoparticles prevented resistance measurements. Based on these findings, it was determined that sensor optimal graphene: TiO$_2$ weight ratio is about 70 graphene nanoplatelets: 30 TiO$_2$ nanoparticles. Consequently, all graphene-TiO$_2$ hybrid materials were then synthesized using a 70:30 graphene to TiO$_2$ weight ratio.

Figure 7:
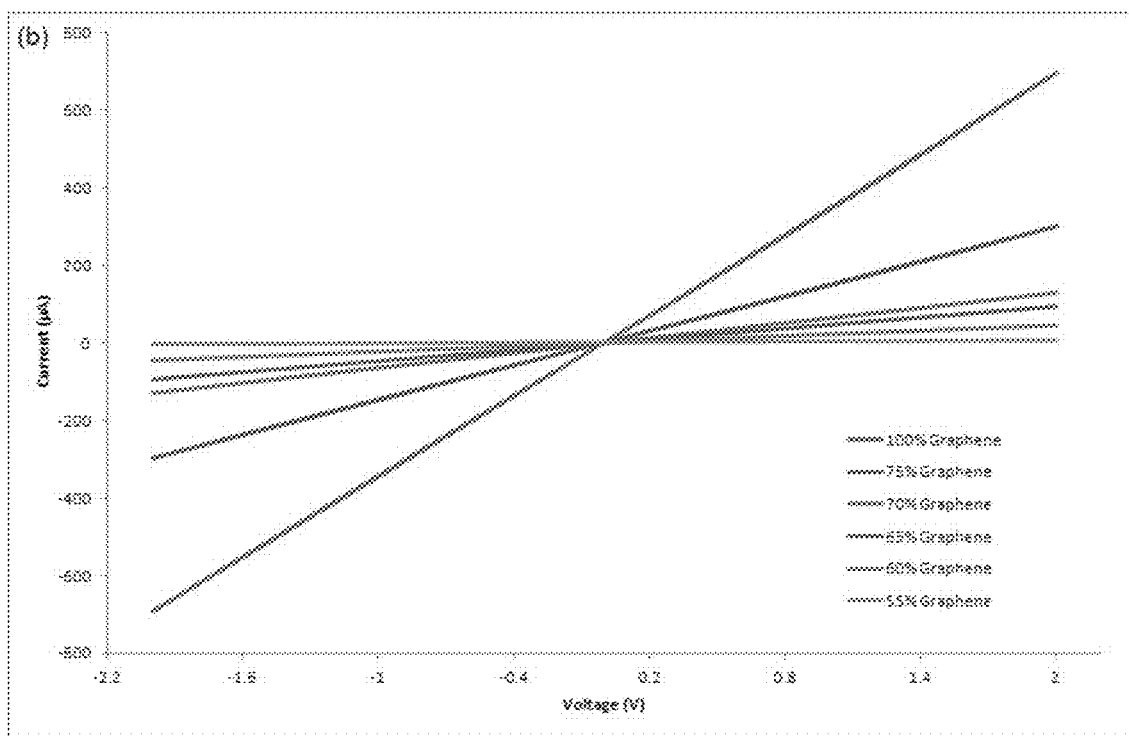
FIG. 7 shows current-voltage characteristic curves for various sensors having different graphene to $TiO_2$ weight ratios. The samples were tested under ambient air with no UV light. The linear relationship between current and applied voltage that was obtained for each sample indicated Ohmic contact between the graphene and the electrodes.
Figure 8:
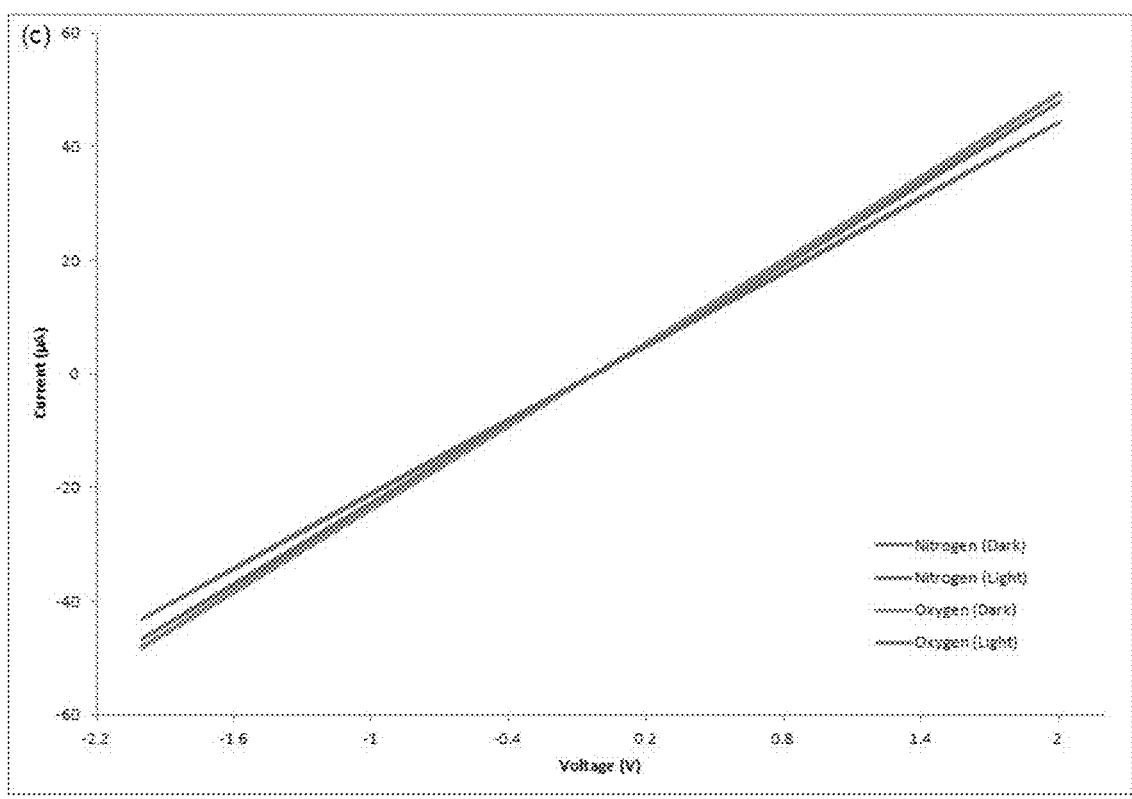
FIG. 8 shows current-voltage characteristic curves for sensors having a 70:30 graphene:$TiO_2$ weight ratio, that were tested in $N_2$ and air under the presence or absence of 365 nm UV light.

FIG. 7 shows current-voltage characteristic curves of several samples obtained under ambient air with no UV light. The linear relationship between current and applied voltage that was obtained for each sample indicated Ohmic contact between the graphene and the electrodes. Tests were also performed on graphene-TiO$_2$ sensors under either N$_2$ or air flow in the presence or absence of exposure to 365 nm UV light, as shown in FIG. 8. No noticeable differences were detected between exposure to N$_2$ and exposure to air in the absence of UV light. These results confirmed that the sensors are insensitive to O$_2$ in the absence of UV illumination. Switching the UV light on caused a 3% decrease in current in samples kept under N$_2$ purging. This change was attributed to the presence of some residual O$_2$ inside the chamber, since vacuum pumping was not utilized. Switching the UV light on caused a 12% decrease in current in samples exposed to air. These results indicated that the sensors are sensitive to O$_2$ gas while under UV illumination.

Example 5: Oxygen Detection

Figure 9:
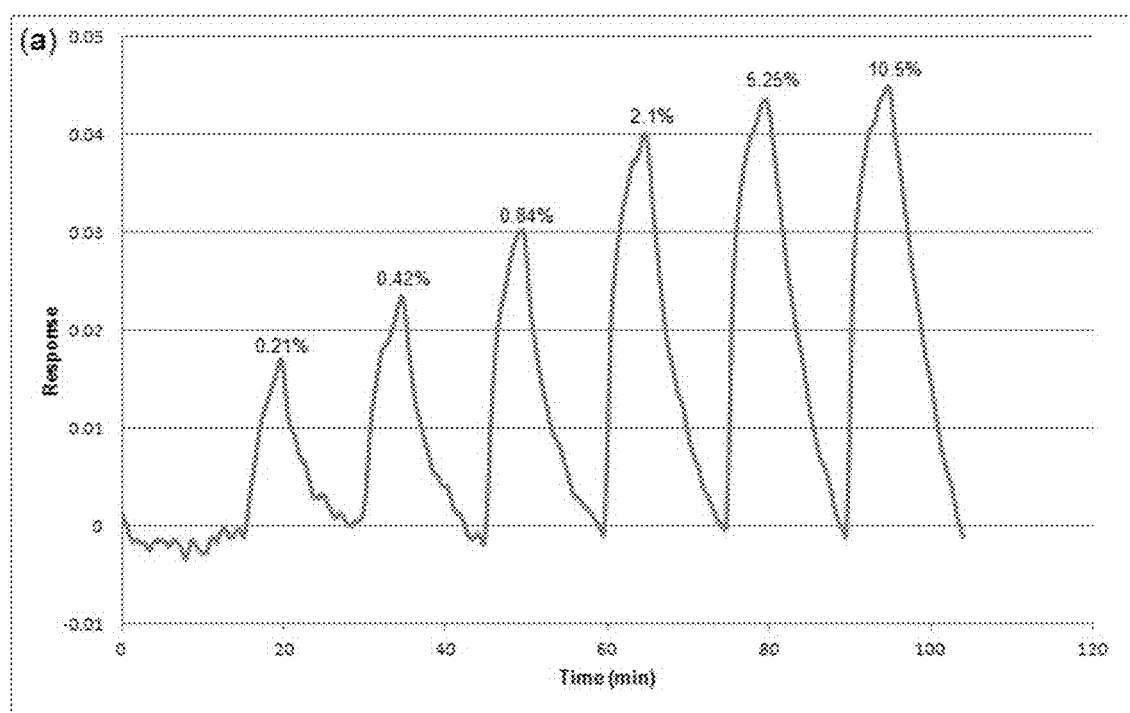
FIG. 9 shows the effect of different oxygen concentrations on sensors' resistance response upon exposure to 365 nm UV light.

To test the ability of the sensors produced as described herein to detect O$_2$ gas, the sensors were exposed to O$_2$ gas emitted from a dry air cylinder in increasing concentrations. Each exposure to O$_2$ lasted five minutes, with ten minutes of purging with N$_2$ gas after each exposure. To set a baseline resistance measurement, the UV lamp was switched on and the sensor was purged with N$_2$ gas for 15 minutes before starting exposure to O$_2$. O$_2$ concentrations ranging from 0.21 to 10.5% v/v were tested. FIG. 9 shows the resulting gas sensing response curve, which was obtained by plotting response signal against time.

The response signal, which is the relative resistance change of the sensor, is defined as: $S=(R-R_0)/R_0$, where $R_0$ is the base resistance of the sensor measured during the initial N$_2$ purge and R is the resistance measured during oxygen exposure. Sensor exposure to O$_2$ gas increased resistance, and sensor purging with N$_2$ gas caused the sensors to recover and decreased sensor resistance to initial baseline levels. As shown in FIG. 10, the magnitude of the response signal was dependent upon the concentration of O$_2$ gas. For O$_2$ concentrations of 0.21 to 21% v/v, a logarithmic trend that relates the O$_2$ concentration (C) to the response signal (S) was calculated as: $S=0.0107 \ln C+0.0321$.

The response signal stopped following this trend once O$_2$ concentration was above 21% v/v. These results indicated that the sensors became likely saturated with O$_2$ molecules. For determination of the detection limits of the disclosed sensors, the minimum true signal was set to be three times the standard deviation of the baseline resistance. Addition of this value to the fitting curve equation resulted in an O$_2$ concentration value of 0.06% v/v, which is the detection limit for the sensors.

Example 6: Sensors' Response and Recovery Time

Figure 11:
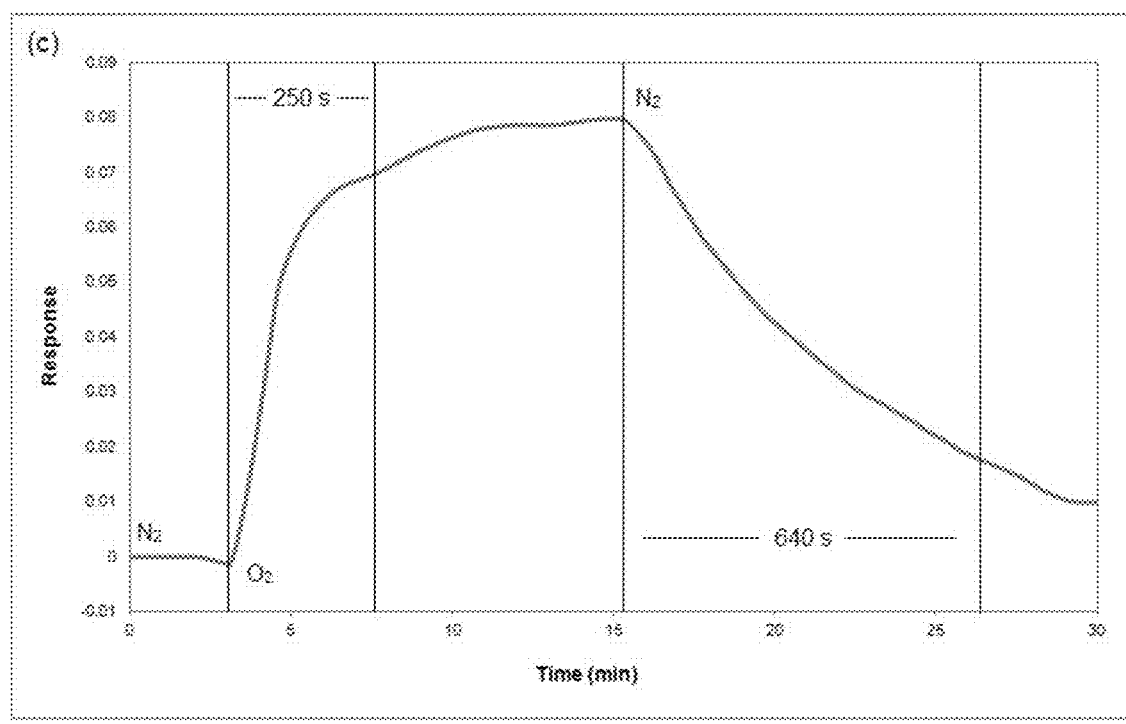
FIG. 11 shows a single sensing cycle curve of 21% v/v $O_2$ used to determine response and recovery time.

The sensors produced as disclosed herein were exposed to 21% v/v O$_2$ gas between N$_2$ purges to determine their response and recovery times. A concentration of 21% v/v O$_2$ gas was selected, as this is the maximal concentration of oxygen that can be obtained from an air source. This concentration was also used to ensure that the sensors would rapidly reach an equilibrium resistance. The response and recovery times were defined as the times needed for the response signal to reach 90% of the equilibrium resistance. As shown in FIG. 11, the sensors showed a response time of 250 seconds and a recovery time of 640 seconds. These response and recovery times are fast for room temperature sensors and could even be improved significantly by heating the sensors.

These response and recovery times were used to set the exposure and purging times for a gas sensing experiment. Sensors that were created using only graphene without the addition of TiO$_2$ did not exhibit any O$_2$ sensitivity even during exposure to 365 nm UV illumination. When graphene and graphene-TiO$_2$ sensors were exposed to O$_2$ without UV illumination, no response was detected. These results confirmed that graphene is not intrinsically responsive to O$_2$, and that UV light is necessary for the graphene-TiO$_2$ sensors to detect O$_2$.

Example 7: Sensors' Sensitivity

Photoexcitation of TiO$_2$ is responsible for sensors' sensitivity to O$_2$, as ultraviolet light excites TiO$_2$ electrons to the conduction band. Electron excitation is brought about by the band gap of anatase TiO$_2$, which is 3.2 eV and corresponds to a peak excitation wavelength of about 385 nm. Electron excitation would increase the conductivity of the sensors under vacuum conditions. However, in the presence of O$_2$ molecules, O$_2$ molecules act as an electron trap when they are adsorbed onto the surface of TiO$_2$ and the reaction $O_2+e^- \rightarrow O_2^-$ occurs. Therefore, sensors' resistance increases as a function of the concentration of O$_2$, as shown above. Surface defects on the TiO$_2$ further increases absorption of O$_2$ molecules. As more O$_2$ molecules adsorb onto the surface, an electron depletion region forms, lowering the conductivity of TiO$_2$. Because of its inherently high carrier mobility and low electrical noise, graphene is sensitive to the changes in conductivity brought about by oxygen adsorption, and since graphene acts as an electron transporter in graphene-TiO$_2$ hybrid materials, excited TiO$_2$ electrons can migrate to graphene through a percolation mechanism.

The results presented herein demonstrate that the overall resistance of the disclosed graphene-TiO$_2$ hybrid sensors increases upon exposure to O$_2$ under 365 nm UV illumination.

Example 8: Exposure to 254 nm UV Light

Figure 12:
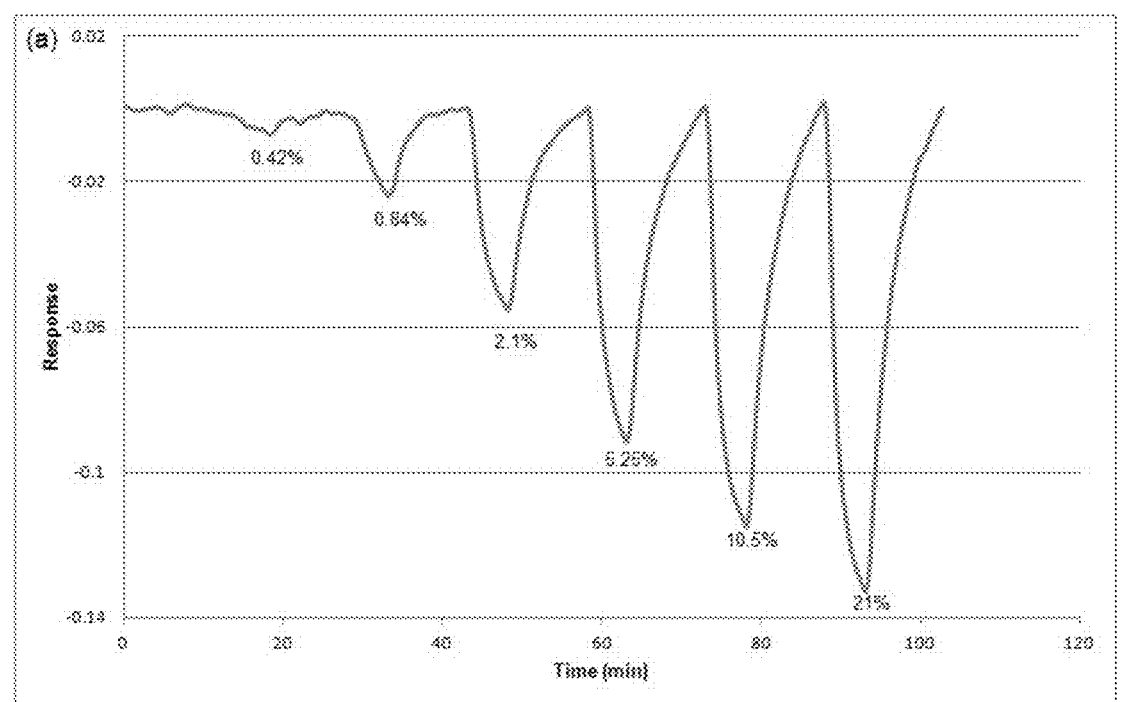
FIG. 12 shows the effect of different oxygen concentrations on sensors' resistance response upon exposure to 254 nm UV light.
Figure 13:
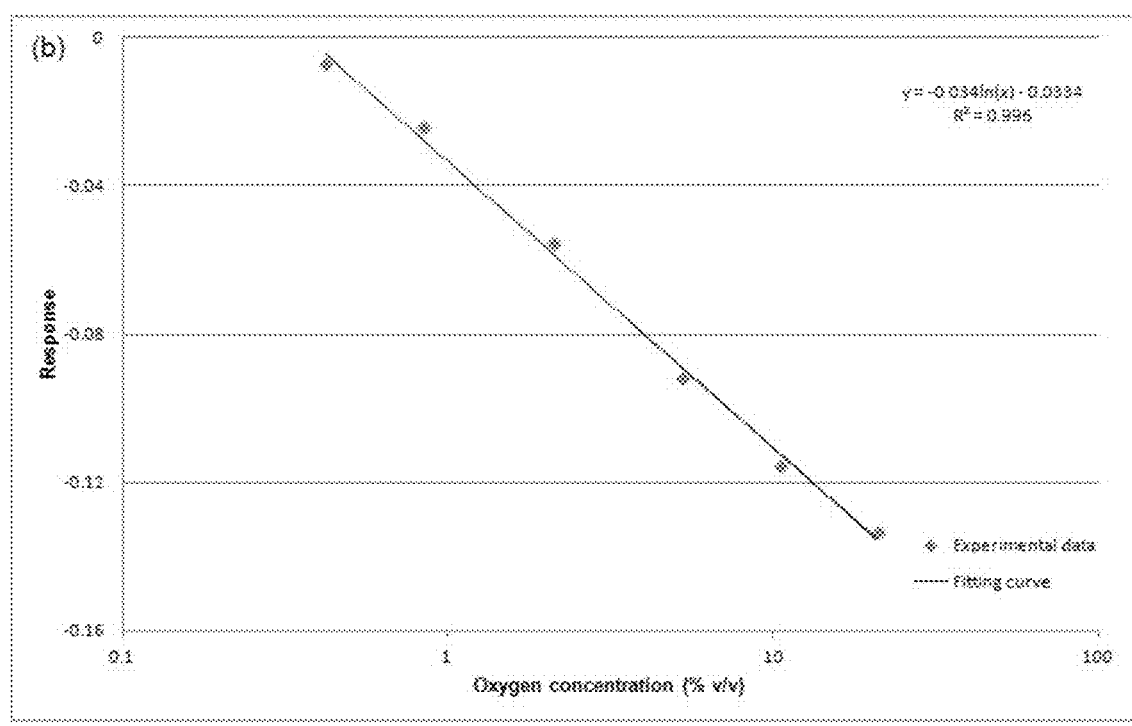
FIG. 13 is a calibration curve derived from the resistance response curve shown in FIG. 12.

To compare the effect of different length UV lights on sensors' oxygen detection, relative resistance changes of various samples were measured prior to and following 5-minute exposure of the sensors to 254 nm UV illumination in ambient air. FIG. 6 shows that the weight ratio of graphene to TiO$_2$ had no effect on resistance changes. Graphene samples free of TiO$_2$ and graphene-TiO$_2$ hybrid samples showed similar resistance patterns, which suggests that graphene is responsible for resistance changes. Gas sensing was then tested under exposure to 254 nm UV illumination. Graphene sensors were exposed to O$_2$ at concentrations ranging from 0.42 to 21% v/v. FIGS. 12 and 13 show that the resistance of the sensors decreased as O$_2$ concentration increased, according to the logarithmic equation: S=−0.34 ln C −0.0334.

Figure 14:
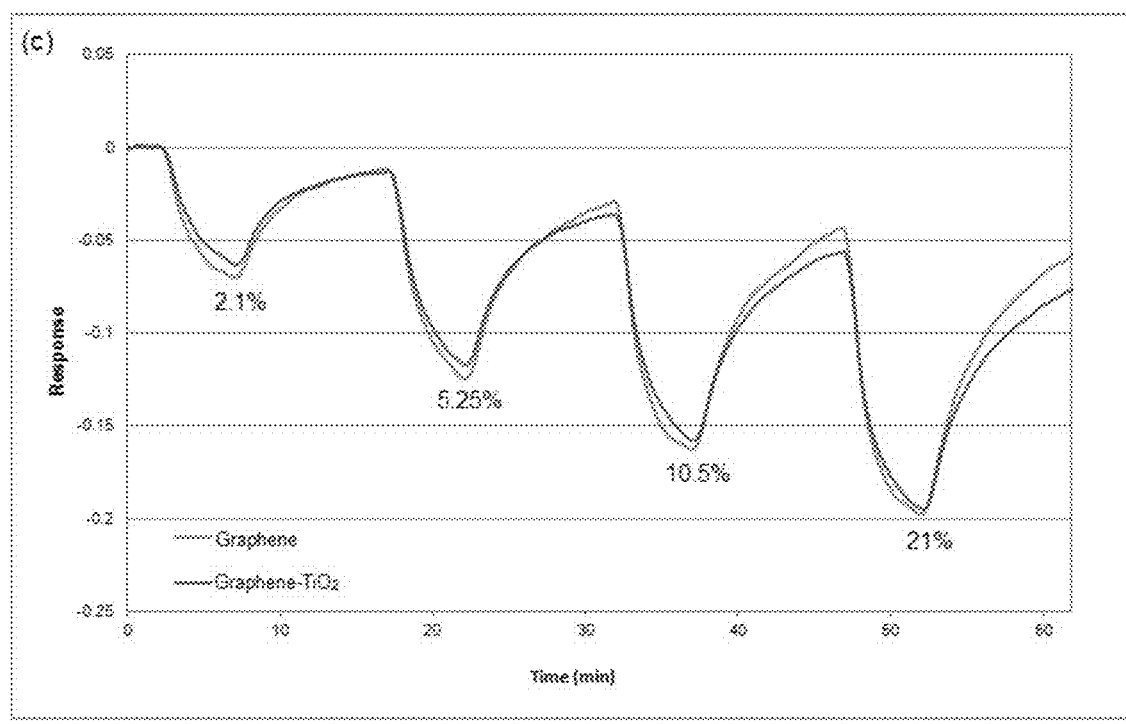
FIG. 14 is a graph comparing the resistance response of graphene and graphene-$TiO_2$ sensors.

The effect of exposure to 254 nm UV illumination on oxygen detection was then determined in graphene-TiO$_2$ sensors, and compared to graphene sensors. The results, which are shown in FIG. 14, indicated no discernible differences in the shape of the response curve and in the relative response between the two types of sensors.

Unlike exposure to 365 nm UV illumination, which caused positive changes in sensors' resistance, exposure of the sensors to 254 nm UV illumination caused negative changes in resistance. These results indicated that an alternate mechanism takes place upon exposure of the sensors to 254 nm UV light, and the addition of TiO$_2$ to graphene does not affect the response of the sensors under 254 nm UV light.

Example 9: Effect of Ozone Production on Sensors' Response

Shortwave mercury vapor UV lamps emit primary light with wavelength of 254 nm, and emit smaller light at 185 nm. This shortwave light generates small concentrations of ozone (O$_3$) from O$_2$ gas. Although unstable atomic oxygen is also generated in this process, atomic oxygen immediately recombines with molecular oxygen or another atomic oxygen to form O$_3$ or molecular oxygen. Therefore, atomic oxygen was not considered a factor affecting sensors' sensitivity.

Figure 15:
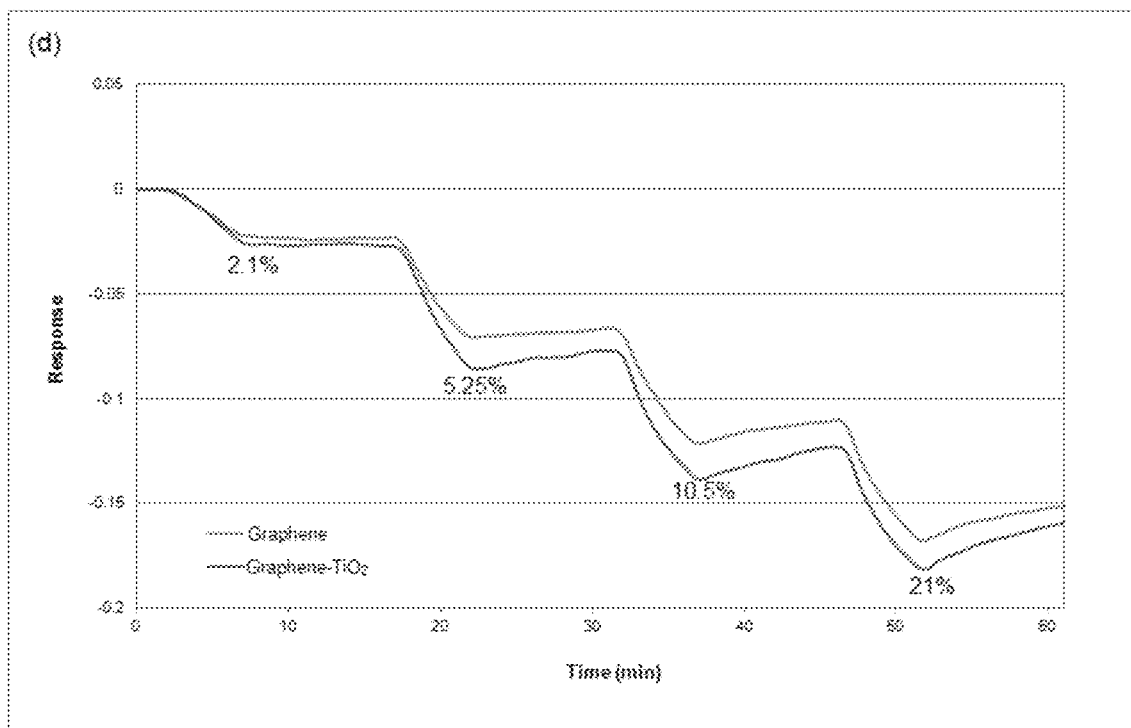
FIG. 15 shows ozone effect on graphene sensors and graphene-$TiO_2$ sensors.

To determine whether the effect of exposure to 254 nm UV light on the disclosed sensors was related to ozone (O$_3$) generation and detection, an assay was designed to separate the effects of UV light on O$_2$ molecules from those on sensors. Graphene and graphene-TiO$_2$ sensors were tested. Air was flown into a chamber in which a black filter capable of adsorbing UV light and allowing gas flow was placed between the UV lamp and each sensor. The UV light generated O$_3$ from O$_2$, and O$_3$ passed through the filter. Because the sensors were not exposed to UV light, the response was solely due to O$_3$ effect. The results, shown in FIG. 15, indicated no significant differences in the shape of the response curve between graphene sensors and graphene-TiO$_2$ sensors. Compared to the results shown in FIG. 14, sensors' response in the absence of UV light irradiation was 10% to 20% lower in magnitude depending on O$_2$ concentration, and the sensors' ability to recover during N$_2$ purging was significantly reduced. These results confirmed that UV irradiation enhances sensors' response and recovery through photo-excitation of TiO$_2$, and also indicated that the disclosed sensors can be used to detect ozone.

Figure 17:
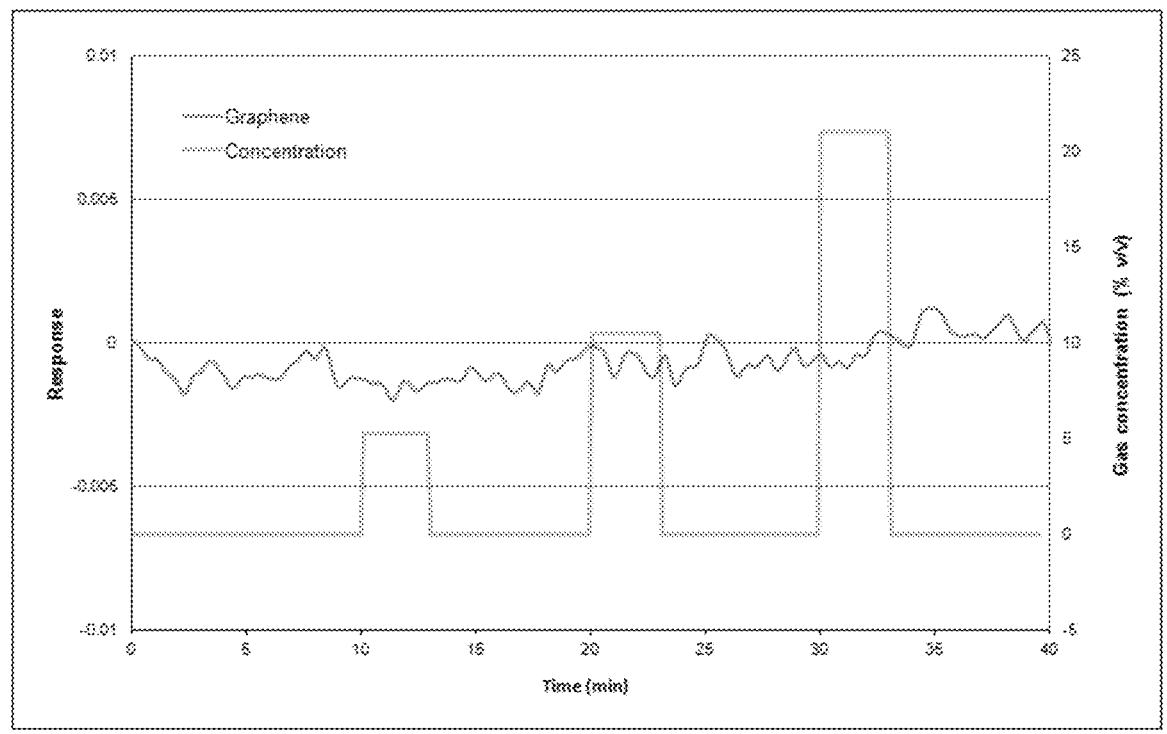
FIG. 17 shows the effect of increasing concentrations of oxygen on graphene-$TiO_2$ sensors from which 365 nm UV light irradiation is blocked. The lack of changes in resistance by the sensors indicates that 365 nm UV light does not produce ozone gas.

Graphene sensors showed no detectable decrease in resistance when tested in the presence of a black filter under 365 nm UV light (FIG. 17). These results demonstrated that the black filter was effective at absorbing incident light, and 365 nm UV light did not generate a measurable quantity of O$_3$.

Example 10: Effect of Carbon Dioxide on Sensors' Activity

Carbon dioxide (CO$_2$) is present in air at a volume fraction of about 400 ppm. To determine the effects of carbon dioxide on the disclosed sensors, the sensors were exposed to increasing concentrations of CO$_2$ (50 ppm, 200 ppm, 500 ppm balanced with air) with air purge under 365 nm UV light. As shown in FIG. 16, graphene-TiO$_2$ sensors exhibited no detectable response to CO$_2$. Resistance drift was caused by O$_2$ adsorption onto the sensors. Argon in air is inert, and the other gases present in air were assumed to have a negligible effect on the sensor because of their presence in minute concentrations. These data confirmed that O$_2$ present in air was the sole gas being detected.

Example 10: Practical Applications

The results presented herein clearly demonstrate that the graphene-TiO$_2$ sensors detect O$_2$ with high precision at volume concentrations below 2.1% v/v upon exposure to 365 nm UV light, and at concentrations above 2.1% v/v upon exposure to 254 nm UV light. Therefore, the disclosed sensors can be used with long wave and short wave UV light sources, which can be alternatively switched and wider range of oxgen can be detected. Light emitting diodes are suitable because of their smaller size, lower power consumption, and better control over the emitted wavelength. Thus, the disclosed sensors have a wide range of detection, a low detection limit, and are produced by cost-effective technology.

It should be recognized that illustrated embodiments are only examples of the disclosed product and methods and should not be considered a limitation on the scope of the invention. Rather, the scope of the invention is defined by the following claims. We therefore claim as our invention all that comes within the scope and spirit of these claims.

EXEMPLARY EMBODIMENTS

Exemplary embodiments provided in accordance with the disclosed subject matter include, but are not limited to, the following:

A gas sensor detecting oxygen gas at room temperature and comprising titanium oxide nanoparticles attached to graphene nanoplatelets.

The gas sensor according to embodiment 1, wherein the graphene nanoplatelets and the titanium dioxide nanoparticles are in a weight ratio from about 55:45 to about 75:25.

The gas sensor according to any of the preceding embodiments, wherein the graphene nanoplatelets and the titanium dioxide nanoparticles are in a weight ratio of about 70:30.

The gas sensor according to any of the preceding embodiments, wherein the sensor is integrated into an artificial intelligence device.

The gas sensor according to any of the preceding embodiments, wherein the sensor has a resistance that changes in oxygen's presence upon exposure to UV light.

A method of producing a gas sensor that detects oxygen gas at room temperature, wherein the method comprises: (i) mixing graphene nanoplatelets and titanium dioxide (TiO$_2$) nanoparticles to obtain a dispersion; (ii) ultrasonicating the dispersion to obtain a homogeneous graphene-TiO$_2$ dispersion; and (iii) drop-casting the homogeneous graphene-TiO$_2$ dispersion onto an integrated drive electronics (IDE) channel on a circuit board sensor chip.

The method according to the preceding embodiment, wherein the graphene nanoplatelets have an average surface area of 600 to 750 m$^2$/g, a thickness of about 5-10 nm, and a diameter of 1-5 μm, and wherein the titanium dioxide nanoparticles have an average particle size of about 5 nm to about 15 nm.

The method according to any of the preceding embodiments, wherein the graphene nanoplatelets and the titanium dioxide nanoparticles are mixed in a weight ratio from about 55:45 to about 75:25.

The method according to any of the preceding embodiments, wherein the graphene nanoplatelets and the titanium dioxide nanoparticles are mixed in a weight ratio of about 70:30.

The method according to any of the preceding embodiments, wherein the method comprises mass-producing the sensor by wafer fabrication.

The method according to any of the preceding embodiments, wherein the sensor changes resistance in oxygen's presence upon exposure to a UV light source.

The method according to any of the preceding embodiments, wherein the method further comprises integrating the sensor into an artificial intelligence device.

A method of detecting an analyte in a gaseous sample at room temperature and ambient pressure, wherein the method comprises: (i) exposing a gas sensor to a gaseous sample, wherein the gas sensor comprises titanium oxide nanoparticles attached to graphene nanoplatelets; (ii) exposing the sensor to UV irradiation at room temperature; and (iii) measuring a change in the sensor's resistance in response to UV irradiation, wherein magnitude of the change in the sensor's resistance is dependent upon the analyte's concentration, thereby detecting the analyte in the gaseous sample.

The method according to the preceding embodiment, wherein the method further comprises determining the concentration of the analyte in the sample according to the logarithmic formula: $S=0.0107 \ln C + 0.0321$, wherein S is the change in the sensor's resistance in response to UV irradiation defined as: $S=(R-R_0)/R_0$, wherein $R_0$ is the sensor's base resistance and R is the sensor's resistance measured during gas exposure, and C is the concentration of the analyte in the gaseous sample.

The method according to any of the preceding embodiments, wherein the method further comprises purging the sensor with nitrogen for a time period from about 1 minute to about 20 minutes to decrease the sensor's resistance to baseline after each exposure to UV light.

The method according to any of the preceding embodiments, wherein the sensor's change in resistance time in response to UV irradiation is about 250 seconds, and wherein the sensor's recovery time is about 640 seconds.

The method according to any of the preceding embodiments, wherein UV irradiation is long wave UV light, and wherein the analyte is oxygen.

The method according to any of the preceding embodiments, wherein the long wave UV light is 365 nm UV light, and wherein the sensor's resistance increases with an increase in oxygen concentration in the gaseous sample.

The method according to any of the preceding embodiments, wherein the oxygen concentration in the gaseous sample is in a range from about 0.06% to about 15% (v/v).

The method according to any of the preceding embodiments, wherein UV irradiation is short wave UV light, and wherein the analyte is oxygen and/or ozone.

The method according to any of the preceding embodiments, wherein the short wave UV light is 254 nm UV light, and wherein the sensor's resistance decreases with an increase in oxygen concentration in the gaseous sample.

The method according to any of the preceding embodiments, wherein the oxygen concentration in the gaseous sample is in a range from about 0.4% to about 21.5% (v/v).

The method according to any of the preceding embodiments, wherein gas flow is kept constant at 400 sc/cm.

The method according to any of the preceding embodiments, wherein the graphene nanoplatelets and the titanium dioxide nanoparticles are in a weight ratio from about 55:45 to about 75:25.

The method according to any of the preceding embodiments, wherein the graphene nanoplatelets and the titanium dioxide nanoparticles are in a weight ratio of about 70:30.

The method according to any of the preceding embodiments, wherein the method comprises alternatively irradiating the sensor with a long wave UV light source and a short wave UV light source.

The method according to any of the preceding embodiments, wherein the long wave UV light is 365 nm UV light, and the short wave UV light is 254 nm UV light, and wherein the UV light source is a light emitting diode (LED).

The method according to any of the preceding embodiments, wherein the sensor is integrated into an artificial intelligence device.

The method according to any of the preceding embodiments, wherein the gaseous sample is a spacecraft sample, a spacesuit sample, a food processing sample, a steel or cement production sample, an ink jet sample, a solution casting sample, a spin-coating sample, a laboratory sample, an electronic fuel injection or emission sample, a medical sample, or a pharmaceutical sample.

The invention claimed is:

1. A method of detecting an analyte in a gaseous sample at room temperature and ambient pressure, wherein the method comprises:
   (i) exposing a gas sensor to a gaseous sample, wherein the gas sensor comprises titanium oxide nanoparticles attached to graphene nanoplatelets;
   (ii) exposing the sensor to UV irradiation at room temperature; and
   (iii) measuring a change in the sensor's resistance in response to UV irradiation, wherein magnitude of the change in the sensor's resistance is dependent upon the analyte's concentration, thereby detecting the analyte in the gaseous sample.

2. The method of claim 1, wherein the method further comprises determining the concentration of the analyte in the sample according to the logarithmic formula:

$$S=0.0107 \ln C + 0.0321,$$

wherein S is the change in the sensor's resistance in response to UV irradiation defined as:

$$S=(R-R_0)/R_0,$$

wherein $R_0$ is the sensor's base resistance and R is the sensor's resistance measured during gas exposure, and C is the concentration of the analyte in the gaseous sample.

3. The method of claim 2, wherein the method further comprises purging the sensor with nitrogen for a time period from about 1 minute to about 20 minutes to decrease the sensor's resistance to baseline after each exposure to UV light.

4. The method of claim 3, wherein the sensor's change in resistance time in response to UV irradiation is about 250 seconds, and wherein the sensor's recovery time is about 640 seconds.

5. The method of claim 4, wherein UV irradiation is long wave UV light, and wherein the analyte is oxygen.

6. The method of claim 5, wherein the long wave UV light is 365 nm UV light, and wherein the sensor's resistance increases with an increase in oxygen concentration in the gaseous sample.

7. The method of claim 6, wherein the oxygen concentration in the gaseous sample is in a range from about 0.06% to about 15% (v/v).

8. The method of claim 4, wherein UV irradiation is short wave UV light, and wherein the analyte is oxygen and/or ozone.

9. The method of claim 8, wherein the short wave UV light is 254 nm UV light, and wherein the sensor's resistance decreases with an increase in oxygen concentration in the gaseous sample.

10. The method of claim 9, wherein the oxygen concentration in the gaseous sample is in a range from about 0.4% to about 21.5% (v/v).

11. The method of claim 4, wherein gas flow is kept constant at 400 sc/cm.

12. The method of claim 11, wherein the graphene nanoplatelets and the titanium dioxide nanoparticles are in a weight ratio from about 55:45 to about 75:25.

13. The method of claim 12, wherein the graphene nanoplatelets and the titanium dioxide nanoparticles are in a weight ratio of about 70:30.

14. The method of claim 13, wherein the method comprises alternatively irradiating the sensor with a long wave UV light source and a short wave UV light source.

15. The method of claim 14, wherein the long wave UV light is 365 nm UV light, and the short wave UV light is 254 nm UV light, and wherein the UV light source is a light emitting diode (LED).

16. The method of claim 15, wherein the sensor is integrated into an artificial intelligence device.

17. The method of claim 16, wherein the gaseous sample is a spacecraft sample, a spacesuit sample, a food processing sample, a steel or cement production sample, an ink jet sample, a solution casting sample, a spin-coating sample, a laboratory sample, an electronic fuel injection or emission sample, a medical sample, or a pharmaceutical sample.

* * * * *